(12) United States Patent
Laudano et al.

(10) Patent No.: US 6,924,361 B1
(45) Date of Patent: Aug. 2, 2005

(54) PHOSPHOPEPTIDE-SPECIFIC ANTIBODIES THAT ARE ACTIVITY SPECIFIC; METHODS OF PRODUCTION AND ANTIBODY USES

(75) Inventors: Andrew Peter Laudano, Durham, NH (US); David Frederick Stern, Madison, CT (US)

(73) Assignee: Phosphoproteomics LLC, Guilford, CT (US)

( * ) Notice: Subject to any disclaimer, the term of this patent is extended or adjusted under 35 U.S.C. 154(b) by 0 days.

(21) Appl. No.: 08/146,235

(22) Filed: Nov. 2, 1993

(51) Int. Cl.$^7$ .............................................. C07K 16/00
(52) U.S. Cl. ............................. 530/388.24; 530/387.1; 530/387.9; 530/389.2; 530/389.1; 530/389.7; 424/130.1; 424/133.1; 424/138.1; 424/140.1; 424/178.1
(58) Field of Search ........................ 530/387.1, 388.24, 530/387.9, 389.2, 389.1, 389.7; 424/130.1, 133.1, 138.1, 140.1, 9, 178.1; 514/8, 23; 435/7.1, 7.2; 436/547, 548

(56) References Cited

FOREIGN PATENT DOCUMENTS

WO    WO93/21230    10/1993

OTHER PUBLICATIONS

Lee et al, Science vol. 251 p. 675, Feb. 1991.*
Roitt et al., Immunology, 3rd Ed., Mosby–Year book Europe Ltd., p. 4.2, 1993.
Epstein, R.J. et al., Synthetic phosphopeptide immunogens yield activation–specific antibodies to the c–erb–B–2 receptor, Proc. Natl. Acad. Sci. vol. 89.,pp. 10435–10439, Nov. 1992.
Glenney, J.R., et al., Monoclonal antibodies to phosphotyrosine. J. Immunol. Mthd. vol. 109, pp. 277–285, 1988.
Keating, M.T., et al., Ligand activation causes a phosphorylation–dependent change in the platelet–derived growth factor receptor conformation. J. Biol. Chem. vol. 263(26) p. 12805–12808, 1988.
Riechmann, L., et al., Reshaping human antibodies for therapy. Nature vol. 332, pp. 323–327.
Queen, C., et al., A humanized antibody tha binds to the interleukin 2 receptor. Proc. Natl. Acad. Sci. vol. 86, pp. 10029–10033.
Seigneurin, J.M., et al., Herpes simplex virus D glycoprotein: Human monoclonal antibody produced by a bone marrow cell line. Science vol. 221, pp. 173–175.
Roussel et al., Abstract from Sixth Annual Meeting on Oncogenes, Jun. 26–30, 1990, Hood College, Frederick, MD: "Antibodies Specific for the Phosphorylated and Non-phosporylated Carboxy Termini of pp60$^{3-src}$".
Roussel, R., M.S. Thesis: University of New Hampshire, Dec., 1990, "Synthetic Phosphopetides Modeled on the Carboxyl Terminus of PP60$^{C-SRC}$: Specific Antibodies, Binding and Effects on Kinase Activity".

* cited by examiner

Primary Examiner—Sheela J. Huff
(74) Attorney, Agent, or Firm—M. Lisa Wilson (57) ABSTRACT

This invention relates to growth regulatory proteins expressed in various disease states, especially receptor tyrosine kinases and similar growth factor receptors. Prior to the Applicants invention, it was not clear that specific antibodies could be generated that recognized peptide epitopes comprising phosphotyrosine in the context of its surrounding amino acid sequence. Applicants generated antibodies to such phosphotyrosine specific peptides, distinct from antibodies that recognize only phosphotyrosine itself. The invention includes methods for producing phosphopeptide specific antibodies by removing contaminating antibody specificities by negative and/or positive selections. Phosphospecific antibodies and their uses in immunodetection, diagnostic or therapeutic applications are also disclosed.

26 Claims, 4 Drawing Sheets

A. – EGF  α-Ppep

B. + EGF  α-Notch

C. + EGF  α-Ppep

D. + EGF  α-Ppep

FIG. 4

PHOSPHOPEPTIDE-SPECIFIC ANTIBODIES THAT ARE ACTIVITY SPECIFIC; METHODS OF PRODUCTION AND ANTIBODY USES

This work was supported in part by grants from the United States government. References cited throughout the application by numbers inside parentheses are listed at the end of the Examples Section. Each reference cited herein is incorporated in its entirety into this application.

FIELD OF THE INVENTION

This invention relates to growth regulatory proteins expressed in various disease or differentiation states, especially receptor tyrosine kinases and similar growth factor receptors, and more particularly to antibodies that specifically recognize various phosphopeptides of these receptors.

BACKGROUND OF THE INVENTION

Cancer: Neoplastic growth of cancer cells results when normal cells have lost their usual control mechanisms for cell growth. Cancer can be induced by multiple factors, including chemical and genetic agents, including in some cases certain viruses. Many different oncogenic retroviruses and DNA tumor viruses are now known that contain oncogenes that are directly responsible for neoplastic transformation of the host cell. These oncogenes frequently encode protein kinases that are enzymes that transfer a phosphate residue from a nucleoside triphosphate to an amino acid side chain of their target proteins. Many retroviral kinases phosphorylate tyrosine residues rather than the serine or threonine residues phosphorylated by most other protein kinases.

In addition to the oncogenes present in tumor viruses, various cells have been shown to express a cellular oncogene counterpart, or proto-oncogene. These cellular genes often encode receptor tyrosine kinases that are important regulators of growth and differentiation (for review, see ref. 1), Activation of these kinases at an inappropriate stage or overexpression may result in neoplastic growth. Thus, the amplification or overexpression of proto-oncogenes has been implicated in the causation of human tumors. For example, c-myc and n-myc proto-oncogenes are amplified in small cell carcinoma of the lung and neuroblastoma, respectively, and alterations in the EGF receptor are frequent in squamous cell carcinoma and glioblastoma.

Tyrosine kinase substrates (the protein targets that get phosphorylated) are integration points for signals that regulate growth and differentiation. Activation of phospholipase C gamma and PI(3) kinase is associated with tyrosinc phosphorylations, as are the MAP (ERK) kinases. Since these substrates regulate key growth and differentiation pathways, their phosphorylation may represent excellent predictive markers for proliferative diseases. Many other receptor systems feed signals into transcription factors that are also activated by tyrosine phosphorylation.

Non-receptor kinases are important in signaling in the immune system (e.g. Ick, lyn, fyn, blk, JAK kinases, src, fgr, Zap-70 and homologs) and in other tissues
neu (also called erbB-2 and HER-2) encodes a 185kDa receptor tyrosine kinase, p185, that is activated by a family of peptides called neu differentiation factor or heregulins (5–8). The four member family includes erbB-2/HER-2 (neu); erbB/HER-l (the epidermal growth factor receptor gene), HER-3, and HER-4. p185 is closely related to the receptor for epidermal growth factor (EGF) (9–11). In general, receptor tyrosine kinases have little basal signaling activity, but are activated weakly by overexpression, and strongly by hormone binding. These protein kinases contain no basal phosphotyrosine in their quiescent state. When activated, they become phosphorylated at several tyrosine residues. Thus, tyrosine phosphorylation characterizes the activated form of the receptors and is essential for normal signaling. The neu protein does not bind the hormone EGF but is activated indirectly by EGF agonists in the presence of the EGF receptor (EGFr) (6, 12, 13).

src. The Rous sarcoma virus (RSV) encodes an oncogene, v-src, that is responsible for tumorigenesis. The normal, nontransforming, cellular homologue is c-src. Both genes encode a 60 kD phosphoprotein, often specified as $pp60^{v-src}$ or $pp60^{c-src}$, respectively, and are phosphorylated on serine and tyrosine residues in vivo. The major site of serine phosphorylation is Ser-17. Phosphorylation of Tyr-416 has been shown to be important for kinase activity and transforming ability. The major site of tyrosine phosphorylation in c-src in vivo is Tyr-527, which is located in the carboxy-terminal "tail" region. Phosphorylation of Tyr-527 negatively regulates the kinase and transforming ability of $pp60^{c-src}$.

Prognostic Value: There is a pressing need for improved prognostic indicators for breast cancer. For example, clinical studies have demonstrated that a subset of axillary node negative breast cancer patients benefit from adjuvant endocrine therapy and chemotherapy. The results of these studies have led to proposals that most axillary node negative breast cancer patients should be considered for adjuvant therapy. However, approximately 70% of breast cancer patients without axillary node involvement survive more than 10 years after surgery without systemic adjuvant therapy. Current diagnostic methods are inadequate to reliably predict the subpopulation of node negative patients that are most likely to experience recurrence and who would benefit from adjuvant therapy. The development of reliable prognostic indicators would allow selective targeting of adjuvant therapy to those patients likely to experience recurrence. Improved prognostic methods to identify those patients likely to be "cured" without adjuvant therapy could spare many women the discomfort, toxicity and expense of unnecessary treatment. There is a need for such prognostic indicators, especially for node-negative women-the roughly 50% of breast cancer patients whose lymph nodes show no sign of cancer spread at the time of their original surgery. New prognostic indicators may also be useful for identification of benign lesions that are at increased risk for becoming malignant.

neu is frequently and specifically amplified in human adenocarcinomas, especially breast carcinoma, ovarian carcinoma, and gastric adenocarcinoma (14–22). In many studies of breast carcinomas, neu amplification was found to correlate with poor prognosis in node-positive patients (e.g., ref. 15). However, the amplification or overexpression of neu is only a poor predictor of clinical course, because of the large overlap in outcome of patients without and with the amplification.

The weak prognostic significance of neu amplification may have a simple explanation: receptor abundance is not a good measure of receptor activity. Receptor tyrosine kinases are activated only weakly by overexpression, but are activated very strongly by hormone binding. The presence of hormones actually reduces the steady-state abundance of receptors through down-regulation. Since receptor tyrosine kinases autophosphorylate when activated, the extent of tyrosine phosphorylation is an excellent indicator of receptor activity. Tyrosine phosphorylation of a specific receptor can be measured by anti-phosphotyrosine [anti-Tyr(P)] sera (refs. 2 and 3; for review, see ref. 4), for example, by immunoblot analysis of cell lysates resolved by protein gels or after immunoaffinity isolation of the protein (12, 23).

A more direct approach would be possible if p185-specific anti-Tyr(P) could be produced, since antisera that recognize specific proteins or peptides only when either are tyrosine-phosphorylated (e.g. activated) should be better indicators of enzymatic activity and hence better predictors of tumor aggressiveness. Such a reagent could be used directly on biopsy specimens to assay p185 activation.

DESCRIPTION OF RELEVANT LITERATURE

Oncogene Peptides.
1. Yanaihara et al., U.S. Pat. No. 4,855,406 issued Aug. 8, 1989, disclose the synthesis of oncogene related peptides and their use to generate specific anti-oncogene antibodies.
2. Carney et al., PCT Patent Publication #WO91/05264 published Apr. 18, 1991 disclose neu-related proteins and their antibodies.
3. Weinberg et al., PCT Patent Publication WO89/10412 published Nov. 2, 1989 disclose neu genes, their expression products and antibodies thereof.

Preparation of Antiphosphotyrosine antibodies: Many Investigators have prepared antibodies that recognize phosphotyrosine. These antiphosphotyrosine antibodies do not select for phosphotyrosine in the context of a particular peptide sequence. The key papers include the following methods for the preparation of anti-phosphotyrosine antibodies:
1. Ross, A. H., et al. (1981) Nature (London) 294, 654–655; Used p-azobenzyl phosphonate (ABP), coupled to Keyhole Limpet Hemocyanin, as an analog of phosphotyrosine to immunize rabbits. The polyclonal antibody reacted with phosphotyrosine but not phosphoserine or phosphothreonine.
2. Frackelton, A. R. Jr., et al. (1983) Mol. Cell. Biol. 3, 1343–1352 and U.S. Pat. No. 4,543,439 issued Sep. 24, 1985; Used p-azobenzyl phosphonate (ABP) as an analog of phosphotyrosine, coupled to Keyhole Limpet Hemocyanin, to prepare monoclonal antibodies. The monoclonal antibody reacted with phosphotyrosine but not phosphoserine or phosphothreonine. However the antibody crossreacted with 5' mononucleotides and extensive dialysis of cell extracts was required.
3. Camoglio, P. M., et al. (1984) EMBO J. 3,483–489; Also used p-azobenzyl phosphonate (ABP) as an analog of phosphotyrosine to prepare polyclonal antibodies. The polyclonal antibody reacted with phosphotyrosine but not phosphoserine or phosphothreonlne. The antibody cross-reacted with nucleotide trlphosphates.
4. Ohtsuka, M. et al. (1984) Int. J. Cancer 34, 855–861; Immunized rabbits and mice with phosphotyrosine coupled to bovine serum albumin or polylysine and isolated antibodies that reacted with phosphotyrosine but not with phosphoserine, phosphothreonine, or nucleotide triphosphates.
5. Eck, B., and Heldin, C. -H (1984) J. Biol. Chem. 259, 11145–11152; Immunized rabbits with phosphotyrosine coupled to immunoglobulins and isolated antibodies that reacted with phosphotyrosine but not with phosphoserine, phosphothreonine, or nucleotide triphosphates.
6. Seki, J., et al. (1986) Cancer Res. 46, 907–916; Immunized rabbits and mice with phosphotyrosine coupled to gamma globulin or Keyhole Limpet Hemocyanin.
7. Pang, D. T., et al. (1985) Arch. Blochem. Biophys. 242, 176–186; Immunized with bromoacetylphosphotyramine-conjugates and affinity purified high affinity polyclonal antiphosphotyrosine antibodies in the presence of high concentrations of phosphate.
8. White, M. F., et al. (1985) Nature (London) 318, 183–186; Immunized with bromoacetylphosphotyramine-conjugates and affinity purified high affinity polyclonal antiphosphotyrosine antibodies in the presence of high concentrations of phosphate. Used these antibodies to identify substrates for the Insulin receptor.
9. White, M. F., et al. (1987) J. Biol. Chem. 262, 9769–9777; Immunized with bromoacetylphosphotyramine-conjugates and affinity purified high affinity polyclonal antiphosphotyrosine antibodies in the presence of high concentrations of phosphate. Used these antibodies to identify substrates for the insulin receptor.
10. Wang, J. Y. J., et al. (1982) J. Biol. Chem. 257, 13181–13164; Used the phosphorylated v-Abl protein expressed in bacteria as an immunogen to obtain antiphosphotyrosine antibodies.
11. Wang, J. Y. J., and Baltimore, D. (1985) J. Biol. Chem. 260, 64–71; Used the phosphorylated v-Abl protein expressed in bacteria as an immunogen to obtain antiphosphotyroslne antibodies.
12. Foulkes, J. G., et al. (1985) J. Biol. Chem. 260, 8070–8077; Used the phosphorylated v-Abl protein expressed in bacteria as an immunogen to obtain antiphosphotyrosine antibodies.
13. Kamps, M. P., and Sefton, B. M. (1988) Oncogene 2, 305–315; Used a polymer of phosphotyrosine, alanine and glycine crosslinked to Keyhole Limpet Hemocyanin to generate antiphosphotyrosine antibodies. These antibodies detected numerous Tyrosine-phosphorylated proteins in cells transformed by the oncoproteins: v-Src, v-Yes, v-Fps, v-Ros, and v-Erb-B.

Preparation of Anti-phosphopeptide, and Anti-dephosphopetide Antibodies:
1. Nairn, A., et al. (1982) Nature 299, 734–736 & Nairn, A. C, and Greengard, P. (1983) Fed. Proc., 42, 3017; Prepared both phospho-selective and dephospho-selective rabbit serum antibodies to G-substrate, a neurone-specific substrate for cyclic GMP-dependent protein kinase. A problem with these antibodies was that there was some crossreactivity (about 5–6%) between the phospho and dephospho-selective antibodies.
2. Saffran, A., et al., (1986) EMBO J. 5, 3175; Prepared antipeptide antibodies against a dephosphorylated segment of the nicotinic acetylcholine receptor. These antibodies preferentially recognized the nonphosphorylated forms of this protein.
3. Smith, S. C., et al., (1987) Biochem. J., 244, 625, Prepared a monoclonal antibody that selectively recognized the phosphorylated form of phenylalanine hydroxylase, as well as a synthetic phosphorylation site peptide.
4. Glass, D. B., and Uphouse, L. A. (1990) in Peptides and Protein Phosphorylation, ed. Kemp, B. M. (CRC Press Inc., Boca Raton), pp 255–287; Prepared antibodies against a major phosphorylation site of L-pyruvate kinase using synthetic peptides as the immunogen or by immunization with the intact protein. Antibodies were isolated by affinity chromatography using the immobilized non-phosphopeptide. Since the peptide used for purification and immunization was non phosphorylated, these antibodies do not discriminate between phospho and dephospho forms.
5. Czernik, A. J., et al., (1991) Methods Enzymol. 201, 264–283; Methods of producing serine and threonine phosphopeptide specific antibodies.

SUMMARY OF THE INVENTION

The Applicants have developed a method to reproducibly produce peptide-specific-phosphopeptide antibodies. Unlike the phospho-tyrosine antibodies of the prior art, which indiscriminately recognize many different proteins that contain a phosphorylated tyrosine group, the antibodies of Applicants' invention recognize phospho-tyrosine only in the context of its surrounding amino acid sequence; e.g. in a peptide specific manner. Thus, the Applicants' antibodies specifically recognize a peptide or protein, only when it is tyrosine phosphorylated; the antibodies do not recognize other tyrosine-phosphorylated peptides and do not recognize the peptide or protein when it is not phosphorylated.

Applicants disclose a method of producing phosphopeptide-specific antibodies comprising the steps of: (a) generating antibodies that are reactive with phosphopeptides; (b) selectively removing nonphosphopeptide-specific antibodies by binding said nonphosphopeptide-specific antibodies to nonphosphopeptide linked to a solid support and recovering the unabsorbed phosphopeptide-specific antibodies; and (c) selectively removing phospho-amino acid specific antibodies by binding the phosphopeptide-specific antibodies so recovered to phospho-amino acid linked to a solid support, and recovering the unabsorbed phosphopeptide-specific antibodies, where steps (b) and (c) can be performed in either order.

Another embodiment of the invention is a method for detecting neoplastic cells in a patient suspected of having a neoplastic disease in which the patient's cells are interacted with phosphopeptide specific antibodies under conditions allowing immunoreactive binding and determining whether binding has occurred, where specific binding is indicative of the presence of neoplastic cells.

Further embodiments of the invention include phosphopeptide-specific antibodies; their fragments; and their uses in immunoassays, as conjugated antibodies, as pharmaceutical compositions, in research or diagnostic kits, and as diagnostic or therapeutic agents.

Abbreviations:
Fab fragment antigen binding
EGF epidermal growth factor
EGFr epidermal growth factor receptor
Tyr(P) phosphotyrosine
anti-Pep(P) antibodies raised against neu phosphopeptide Tyr(P)-1248 and affinity purified as described
anti-Tyr(P) anti-phosphotyrosine
CSF-1 colony-stimulating factor 1
PDGFr platelet-derived growth factor receptor
MGF mast-cell growth factor.
neu HER-2 or erbB-2 or p185
c-kit MGF receptor
c-met the scatter factor receptor

BRIEF DESCRIPTION OF THE DRAWINGS

FIG. 1 Immunoblot analysis with anti-Tyr(P) and anti-Pep(P). Cells were treated with growth factors and immunoprecipitated with anti-receptor antisera. The samples were divided into equal portions, resolved by SDS/polyacrylamide gel electrophoresis, and examined by immunoblot analysis with anti-Tyr(P) (A), anti-Pep(P) (B), or anti-Pep(P) preincubated with blocking agents (C-F). Immunoprecipitates were prepared from mock-treated (m, lanes 1) or MGF-treated (lanes 2) 624 mel human melanoma cells with antis-kit; mock-treated (lanes 3) or PDGF-treated (lanes 4) C127 mouse fibroblasts with anti-PDGF receptor; mock-treated (lanes 5 and 7) or EGF-treated (lanes 6 and 8) SK-BR-3 human breast carcinoma cells immunoprecipitated with anti-p185 (lanes 5 and 6) or anti-EGFr (lanes 7 and 8). Samples were analyzed on an immunoblot with affinity-purified anti-Tyr(P) (A) or anti-Pep(P) (B). (C–F) Anti-Pep (P) (7.8 ug in 0.46 ml) was incubated for 10 min on ice with the following competing reagents and then diluted 1:10 to yield the same final concentration as for B: 0.65 mM nonphosphorylated neu peptide (C), 10 mM Tyr(P) (D), nonphosphorylated peptide plus Tyr(P) (E), or 0.65 mM phosphorylated neu peptide (F). Autoradiographs were exposed overnight (A) or for 4 days (B–E) to Kodak X-Omat AR film with an intensifying screen at −70° C. Asterisk, MGF receptor (c-kit); boxes, PDGF receptor; triangles, p185; circles, EGFr. The electrophoretic mobilities and nominal molecular masses of prestained standards (Bethesda Research Labs) are indicated at left in kDa. IP, immunoprecipitate.

FIG. 2. Immunoblot analysis of receptors and cell lysates. Immunoprecipitates were prepared with anti-insulin receptor antibody from NIH 3T3 cells treated with insulin (lanes 1) or mocktreated (m, lanes 2), with anti-c-met from 624 mel cells treated with scatter factor (SF, lanes 5), or with anti-EGFr from SK-BR-3 cells treated with EGF (lanes 10). Lysates were prepared from pZen cells treated with CSF-I (lanes 3) or mock-treated (lanes 4), C127 cells treated with PDGF (lanes 6) or mock-treated (lanes 7), or SK-BR-3 cells treated with EGF (lanes 8) or mock-treated (m, lanes 9). Lysates in lanes 6–9 had been partly immunodepleted of the PDGFr (lanes 6 and 7) or p185 (lanes 8 and 9) with limiting amounts of antibody. Replicate samples were analyzed on an immunoblot with anti-Tyr(P) (A) or anti-Pep(P) (B) preincubated with the nonphosphorylated neu peptide as described for FIG. 1C. Each panel is a composite of three portions derived from a single original gel and filter. (A) Exposed for 6 days after two $^{125}$I half-lives had elapsed. (B) Exposed for 6 days with an intensifying screen at −70° C. Bracket, insulin receptor β subunit; +, CSF-1 receptor; solid triangle, scatter factor receptor β subunit; box, PDGF receptor; open triangles, p185; open circles, EGFr; IP, immunoprecipitate; lys, lysate.

FIG. 3. Immunoblot analysis of rodent fibroblasts. Lysates were prepared from FR3T3 rat fibroblasts that had been mock-treated (m) or treated with EGF. They were analyzed on an immunoblot with anti-Tyr(P) (A) or anti-Pep(P) (B). Autoradiographs were exposed overnight (A) or for 10 days (B) with an intensifying screen at −70° C. Circles mark the position of the EGFr.

DETAILED DESCRIPTION OF THE INVENTION.

Methods of Producing Desired Antibodies.

Applicants disclose methods of producing phosphopeptide-specific antibodies as follows:

A method of producing phosphopeptide-specific antibodies comprising the steps:
(a) generating antibodies that are reactive with phosphopeptides;
(b) selectively removing nonphosphopeptide-specific antibodies by binding said nonphosphopeptide-specific antibodies to nonphosphopeptide linked to a solid support and recovering the unabsorbed phosphopeptide-specific antibodies; and
(c) selectively removing phospho-amino acid specific antibodies by binding the phosphopeptide-specific antibodies so recovered to phospho-amino acid linked to a solid support, and recovering the unabsorbed phosphopeptide-specific antibodies, where steps (b) and (c) can be performed in either order. Steps (b) and (c) can be done in either order; e.g. first negatively selecting for peptide-specific. antibodies followed by negatively selecting for phospho-amino acid specific antibodies; or first negatively selecting for phospho-amino acid specific antibodies followed by negatively selecting for peptide-specific antibodies.

In a further embodiment of the invention, Applicants disclose a method of producing phosphopeptide-specific antibodies comprising a positive selection step:

(d) selecting for phosphopeptide-specific antibodies by binding them to phosphopeptide or phosphoprotein linked to a solid support; and selectively recovering the phosphopeptide-specific antibodies by eluting them from the solid support;

where steps (b), (c) and (d) can be done in any order; but preferably step (d) occurs last.

In another embodiment of the invention, Applicants disclose a method of producing phosphopeptide-specific antibodies comprising a further step:

(e) selectively removing carrier-specific antibodies by binding said carrier-specific antibodies to carrier linked to a solid support and recovering the unabsorbed phosphopeptide-specific antibodies;

where steps (b). (c), (d) and (e) can be done in any order; but preferably step (d) occurs last and step(e) occurs first.

Applicants disclose methods of producing nonphosphopeptide-specific antibodies as follows:

A method of producing nonphosphopeptide-specific antibodies comprising the steps:

(a) generating antibodies that are reactive with nonphosphopeptides;

(b) selectively removing phosphopeptide-specific antibodies by binding said phosphopeptide-specific antibodies to phosphopeptide linked to a solid support and recovering the unabsorbed nonphosphopeptide-specific antibodies; and (c) selectively removing phospho-amino acid specific antibodies by binding the nonphosphopeptide-specific antibodies so recovered to phospho-amino acid linked to a solid support, and recovering the unabsorbed nonphosphopeptide-specific antibodies, where steps (b) and (c) can be performed in either order.

Steps (b) and (c) can be done in either order; e.g. first negatively selecting for phosphopeptide-specific antibodies followed by negatively selecting for phospho-amino acid specific antibodies; or first negatively selecting for phosphoamino acid specific antibodies followed by negatively selecting for phosphopeptide-specific antibodies.

In a further embodiment of the invention, Applicants disclose a method of producing nonphosphopeptide-specific antibodies comprising a positive selection step:

(d) selecting for nonphosphopeptide-specific antibodies by binding them to nonphosphopeptide or nonphosphorylated protein linked to a solid support; and selectively recovering the nonphosphopeptide-specific antibodies by eluting them from the solid support;

where steps (b), (c) and (d) can be done in any order; but preferably step (d) occurs last.

In another embodiment of the invention, Applicants disclose a method of producing nonphosphopeptide-specific antibodies comprising a further step:

(e) selectively removing carrier-specific antibodies by binding said carrier-specific antibodies' to carrier linked to a solid support and recovering the unabsorbed nonphosphopeptide-specific antibodies;

where steps (b), (c), (d) and (e) can be done in any order; but preferably step (d) occurs last and step(e) occurs first.

Solid supports, include but are not limited to, sepharose, polyacrylamide or agarose based matrixes; polypropylene, polystyrene or glass beads; or nitrocellulose based supports. Positive or negative selection steps can be done in a batch format, using beads, for example, or by sequential column chromatography steps, or by combinations of the two.

Peptides. The phosphopeptide or nonphosphopeptides that are linked to the solid support and used for the positive or negative selection steps, can be either chemically synthesized, recombinantly produced peptides or proteins (e.g. in bacteria, yeast, insect or mammalian expression systems), enzymatically phosphorylated peptides or proteins, or naturally purified peptides or proteins. Anti-phosphospecific peptide antibodies of the invention can be produced from any peptide sequence that contains any amino acid residue that can be phosphorylated, including tyrosine, threonine, serine or histidine. The choice of the amino acid sequence surrounding the phosphorylation site to be included in the peptide can be selected to be specific to only I protein or to one or more proteins. The size of the peptide needs to be sufficient to generate an immune response when coupled with a carrier and injected into a host animal, so its shortest length is about 6 amino acid residues (e.g. the size of an antigenic epitope). The upper size of the peptide is not critical, as long as the phosphorylated residue is still accessible to the host animal's immune system. Peptides from the C-terminus are preferred, since they are generally in an exposed configuration and are accessible.

The number of steps in the process should be sufficient to generate antibodies of a specific reactivity, substantially free from any contaminating reactivities. In theory, only a positive selection step is necessary to obtain antibodies of the desired reactivity. In practice, although a one step procedure gives substantial purification of the desired antibody, the antibody may still be contaminated with minor percentages of antibodies exhibiting other reactivities. To eliminate these cross-reactivities, Applicants invention provides for a minimum of two and up to 4 selection steps, employing both positive and negative selections. If it is possible to eliminate steps (d) or (e) and still obtain a desired antibody reactivity, this is a preferred method. One skilled in the art will know how to measure the antibody obtained after each step by any number of different assays to determine whether cross-reacting specificities are present and that the further steps are necessary.

II. Antibodies. Another embodiment of Applicants' invention is phosphopeptide-specific antibodies, and their fragments, as compositions of matter. These antibodies can be either monoclonal or polyclonal. If polyclonal, the antibodies can be produced in any of a wide variety of different species, including but not limited to, mice, rats, rabbits, guinea pigs, goats, primates. or sheep. The selection of a particular host animal will depend in part upon the amino acid sequence of a desired peptide, and whether it will be immunogenic in that host. For example, an animal that already expresses its own peptide that is substantially similar in sequence to the peptide immunogen, may not generate a sufficient immune response to produce antibodies to the immunized peptide. Such considerations are well known to skilled artisans; as are techniques for conjugating peptides to carrier proteins, immunizing with various adjuvants, and testing for antibody production using a wide variety of assays, for example, detecting positive binding to radiolabeled peptides used as the immunogen. Monoclonal antibodies can be produced by standard procedures, such as by Kohler & Milstein (62) with limiting dilution to obtain individual subclones. Screening procedures for detecting monoclonal antibodies are also well-known. Polyclonal or monoclonal antibodies obtained through these means can be positively and/or negatively selected by Applicants' methods as provided above.

Specific embodiments of the antibodies of the invention include the following phosphopeptide and nonphosphopeptide specific antibodies:

(1) Tyr(P)-1248 phospho-neu-specific antibody, (2) Tyr(P)-416 phospho-src-specific antibody, (3) Tyr(P)-523 phospho-c-Fgr-specific antibody, (4) Tyr(P)-505 phospho-Lck-specific antibody, (5) Tyr(P)-751 phospho-PDGFβ-receptor specific antibody, (6) Tyr(P)-857 phospho-PDGFβ-receptor specific antibody, (7) Ser(P)-259 phospho-Raf-1 specific antibody (8) Tyr-1248 nonphospho-neu-specific antibody, (9) Tyr-416 nonphospho-src-specific antibody, (10) Tyr-523 nonphospho-c-Fgr-specific antibody, (11) Tyr-505 nonphospho-Lck-specific antibody, (12) Tyr-751 nonphospho-PDGFβ-receptor specific antibody, (13) Tyr-857 nonphospho-PDGFβ-receptor specific antibody, and (14) Ser-259 nonphospho-Raf-1 specific antibody.

The antibodies of the invention include intact antibodies as well as antibody fragments, including but not limited to, Fab, F(ab'), F(ab')$_2$, Fc, Fv, V (variable), D (Diversity), J (Joining), C (constant), single chain antibodies, H (heavy chain), L (light) chain, λ (lambda light chain), κ (kappa light chain) regions, hinge, framework, and cdr (hypervariable or complementarity) regions. Individuals skilled in the art will be aware of many different mechanisms to generate desired fragments depending upon their prospective use. For example, specific regions can be chemically synthesized; Fab and Fc portions can be generated by enzymatic cleavage using papain; F(ab')$_2$ portions can be generated by enzymatic cleavage with pepsin; H and L chains can be produced by reduction of disulfide bonds; and fragments can be produced by recombinant DNA methods. These procedures are well known in the art.

The antibodies of the invention also include any of the various subclasses of antibodies, including but not limited to, IgM, IgA, IgE, IgD, IgG, IgG1, IgG2, IgG3, IgG4, IgG2a, and IgG2b. Preferably the antibodies have a strong binding affinity, e.g. IgG subclass, to be useful for in vitro or in vivo diagnostic applications. Depending upon the prospective use of the antibodies, it is well known to one in the art, which effector function (constant region) is preferred. For example, IgM, IgG1, IgG3 and IgG2 are effective in activating the complement cascade, while IgG4, IgA, IgD and IgE are ineffective in this respect.

Conjugated antibodies are another embodiment of Applicants' invention. Such conjugates, include but are not limited to, (1) antibodies conjugated to a detectable label for radioimmunodetection, in vivo radioimaging or in vivo radiotherapy (63); radioactive isotopes include, but are not limited to, $^{125}$I, $^{14}$C or $^{3}$H for in vitro studies; $^{123}$I, $^{125}$I, $^{131}$I, $^{99m}$Tc, $^{67}$Ga, $^{90}$Y, $^{111}$In; and $^{186}$Re for in vivo imaging or therapy, (2) antibodies conjugated to an enzyme or enzyme system (horse-radish peroxidase, biotin-streptavidin), (3) antibodies conjugated to a fluorophore, e.g. fluorescein, umbelliferone, phycobiliproteins, or rhodamine (4) antibodies conjugated to a chemiluminescent agent, (5) antibodies conjugated to a toxin, such as ricin, pokeweed antiviral protein PAP, or diphtheria toxin, (6) antibodies conjugated to other antibodies, such as bifunctional antibodies (one antibody to target, the other to "act"), an anti-idiotypic antibody or a anti-constant region antibody, and (7) antibodies conjugated to a chemotherapeutic drug, including but not limited to, vincristine, methotrexate, chlorambucil, adriamycin, mitomycin C, daunomycin, etoposide, azidothymidine, thiogoanine, (8) antibodies conjugated to a lymphotoxin or a cytokine, and (9) antibodies conjugated to particles, such as magnetic particles, glass particles, latex particles, or carbon particles.

Methods of conjugation are well known in the art, and include, but are not limited to, aldehyde-derived linkage, using, for example, glutaraldehye; succinimide-derived linkage through amine groups; hydrazide-derived linkage through carbohydrate groups; carbodiimide coupling via aldehydes and carboxyl groups; and malemide and iodoacetyl coupling via sulfhydryl groups. Homobifunctional or heterobifunctional crosslinkers or spacers can be employed.

Immunoassays. The antibodies of the invention can be used in a wide variety of assays, including but not limited to enzyme immunoassay (EIA), enzyme linked immunoabsorbent assay (ELISA), radioimmunoassay (RIA), immunoblot, Western, immunoprecipitation, immunofluorescence, and immunohistochemistry (frozen and paraffin-embedded tissue) assays. These assays can be either competitive or non-competitive, one-step or multiple step assays. There are numerous examples of different assay configurations in the prior art, and one skilled in the art would know which assay to choose for a particular purpose.

Kits. Antibodies of the invention may be included in a kit, together with other reagents necessary for detecting the presence, in vitro or in vivo, of a phosphopeptide in question. Such kits may include reagents necessary for labeling the antibody, for detecting bound antibody, for permeabilizing cells to allow entrance of the antibody into the intracellular domain, and include, but are not limited to, buffers, standards, radionuclides, enzymes, enzyme substrates, salts, chromophores, etc.

Diagnostic & Monitoring Methods. The most significant application for tyrosine phosphopeptide-specific antisera will be the measurement of phosphorylation in tissues in order to correlate the level of phosphorylation with disease state to generate improved prognostic indicators to diagnose disease, to monitor disease progression, or to monitor the efficacy of different therapies. The antibodies of this invention were shown to work in cell-based assays (immunofluorescence and immunohistochemistry) and in tissue-based assays (immunohistochemistry on frozen and paraffinembedded tissue).

Thus, a further embodiment of the invention is a method for diagnosing disease state or immune dysfunction in a patient having a neoplastic disease or immune disorder in which the patient's cells are interacted with a phosphopeptide specific antibody or antibody fragment under conditions allowing immunoreactive binding and determining whether binding has occurred, where specific binding is indicative of disease state or immune dysfunction. Such a method is useful in cancer diagnosis and in monitoring disease progression or therapy outcome.

Using the methods of producing phosphopeptide-specific antibodies disclosed herein, it is possible without undue experimentation to generate similar antibody reagents to other tyrosine, serine, threonine or histidine phosphorylation sites that may be used to identify additional prognostic indicators in other cancers or states of immune system dysfunction. The phosphopeptide-specific antibodies of the invention can also be used for screening for inhibitors of specific tyrosine kinases and for identifying the substrates of these kinases, which may in themselves provide additional, valuable prognostic indicators.

Therapeutic Antibodies of the invention include conjugated antibodies as provided above, as well as chimeric (human C region and non-human V region) antibodies, human (produced from SCID mice or gene knock-out animals) antibodies and humanized (cdr or hypervariable region grafting) antibodies. The human and humanized antibodies being preferred, as they should not elicit a HAMA (human anti-mouse antibody) type response which limits an antibody's utility. Certain classes of murine antibodies, IgG2a, are also more effective at ADCC (antibody-dependent-cell-mediated cytotoxicity) than others, and are preferred. Human antibodies are further preferred, since they should more efficiently mediate ADCC and complement dependent cytolysis. Monoclonal antibodies are preferred for therapeutic utility, since their use minimizes the induction of an immune response in the patient Pharmaceutical compositions are used for in vivo diagnostic (imaging) and therapeutic embodiments of the invention and comprise the functional antibody component (e.g. antibody or conjugate) together with a physiologically acceptable media, including, but not limited to, deionized water, distilled water, buffered saline, saline, amino acid or sugar stabilizers such as mannose, etc. Pharmaceutical compositions can be delivered by well-known techniques in the art, including but not limited to, intravenous injection, liposome delivery and direct injection into tumors. Monoclonal antibodies are preferred for in vivo applications, however, a cocktail of antibodies that recognize different epitopes can be used in other embodiments of the invention.

Therapeutic Methods employ pharmaceutical compositions comprising the antibodies of the invention that act alone via passive immunotherapy or via active therapy, e.g. radioimmunotherapy or immunotoxin therapy.

The therapeutic or diagnostic methods and pharmaceutical compositions of the subject application can be for the benefit of man or animals, as Applicant's antibodies and methods have veterinary and human utility.

Drug Screening. Yet another embodiment of Applicants' invention is a method to be used to screen potential drug candidates for ones that can inhibt or others that can activate the phosphorylation of specific proteins or peptides. In the method, cells are interacted in the presence of a drug, or drugs, with a phosphopeptide-specific-antibody or antibody fragment under conditions allowing immunoreactive binding, and the amount of binding that occurs is measured and compared to the amount of binding that occurs without the drug, where a difference in the amounts so detected is indicative of the drug's action.

EXAMPLES

The invention is further illustrated by the following examples. Rabbits were immunized with a synthetic phosphopeptide corresponding to a major autophosphorylation site of $p185^{neu/erbB2}$ to determine the feasibility of producing tyrosine-phosphopeptide-specific antibodies. A series of adsorption and affinity chromatography steps were used to select antibodies with the desired reactivity [Example 1]. Immunoblot experiments showed that the resulting antibody is highly specific for tyrosine-phosphorylated forms of p185 and the related epidermal growth factor receptor [Example 2]. The antibody recognized these two receptors selectively when compared to five other receptor tyrosine kinases and several phosphorylated substrates [Example 2 & 3]. The antibody is sensitive enough to detect baseline (endogenous) levels of EGF-activated-EGFr in rodent fibroblasts by immunoblot analysis and to recognize activated p185 by immunofluorescence at levels found in SK-BR-3 breast carcinoma cells [Examples 4 & 5]. The antibody is compatible with tissue based assays [Examples 5 & 6], since it detected tyrosine phosphorylation of the epidermal growth factor receptor in immunofluorescence experiments on permeabilized cells [Example 5]. In addition to polyclonal antibodies, monoclonal antiphosphopeptide specific antibodies were generated [Examples 7 & 8]. The generality of the procedures used means that similar anti-tyrosine phosphopeptide sera can be produced that recognize other tyrosine kinases and substrates [Example 9].

Example 1

Tyrosine-phosphopeptide-specific Antisera: Anti-pep (P) Production and Purification Tyrosine-Phosphopeptide-Specific Antisera. A peptide corresponding to a major autophosphorylation site of human neu was chemically synthesized with Tyr(P) incorporated during synthesis, as follows. The phosphorylation site chosen is located near the C terminus of p185 (Tyr(P)-1248). It is similar in sequence to an autophosphorylation site in the closely related EGFr (TAENPEY*LGLDVPV in human p185 vs. TAENAEY*LRVAPQS in EGFr, where the asterisk indicates the autophosphorylation site) but quite different from major autophosphorylation sites of the PDGF, insulin, and CSF-1 receptors and tyrosine phosphorylation sites of substrates including mitogen-activated protein kinases, phospholipase C-γ, and $pp34^{cdc2}$ (refs. 36, 44–53; for review, see ref. 54).

(1) Peptide Synthesis. The O-Tyr(P)-containing peptide Lys-Thr-Ala-Glu-Asn-Pro-Glu-Tyr (P)-Leu-[$^{14}$C]Gly-Leu-Asp-Val-Pro-Val, which corresponds to the phosphorylated C terminus of human neu plus an N-terminal lysine for coupling (36), and the corresponding nonphosphorylated peptide were synthesized by standard Merrifield solid-phase procedures with N-tert-butyloxycarbonyl (Boc) amino acids (37, 38). Boc-O-(dibenzylphosphono)-L-tyrosine (Peninsula Laboratories) was used for incorporation of Tyr(P). The nonphosphorylated peptide was cleaved from the resin for 30 min at room temperature with trifluoromethanesulfonic acid (TFMSA) (39). The phosphorylated peptide was cleaved from the resin with TFMSA as follows: Phosphorylated peptide resin (1 g) was stirred for 10 min at 0° C. with 2 ml of m-cresol and 2 ml of dimethyl sulfide. An ice-cold mixture of 4 ml of TFMSA and 10 ml of trifluoroacetic acid was added slowly with stirring. The reaction was stirred under a nitrogen atmosphere for 4 h at 0° C. The cleaved phosphopeptide was precipitated with methyl tert-butyl ether at −30° C. (39), dissolved in 40% acetic acid, and lyophilized several times from water. The peptide was purified by ion exchange and gel filtration chromatography or by reverse phase high pressure liquid chromatography. (2) Antibody Production & Purification. The phosphorylated neu peptide was coupled to bovine serum albumin with glutaraldehyde and used to immunize rabbits (40). Antisera were initially screened for the ability to immunoprecipitate the phosphorylated and nonphosphorylated peptides labeled with $^{125}$I-labeled Bolton-Hunter reagent (DuPont/NEN).

The peak antisera from rabbit 98 were affinity-purified in two ways: For FIGS. 1 and 2, 6 ml of serum was first passed through a bovine serum albumin-agarose precolumn (Albumin-agarose; Sigma). The flow-through was passed five times through a column of the nonphosphorylated neu peptide linked to Affi-Gel 10 to remove antibodies that recognize the peptide. The column was regenerated by washing with 3 M sodium thiocyanate and equilibrated with phosphate-buffered saline (PBS) prior to each cycle. The flow-through was then applied to a column containing the phosphorylated neu peptide linked to Affi-Gel 10 (BioRad). The column was washed with PBS, bound antibodies were eluted with a step gradient of 3.5 M and 4.5 M $MgCl_2$ in 10 mM sodium phosphate buffer (pH 7.2), and the eluates were dialyzed in Spectrapor 2 tubing (Spectrum) against PBS at 4° C. for 2 days. Since these sera were found to contain residual Tyr(P) immunoreactivity, they were purified by four serial adsorptions to Tyr(P) linked to Affi-Gel 10 and equilibrated with TN (50 mM Tris-HCI, pH 7.4/150 mM NaCl) (35). In a more streamlined procedure (see FIGS. 3 and 4), columns were linked in the following series: 3 ml of bovine serum albumin-agarose, 5 ml of Tyr(P) coupled to AffiGel 10, and 4 ml of nonphosphorylated neu peptide coupled to AffiGel 10. Before use the columns were washed with 30 ml of 3 M sodium thiocyanate and equilibrated with PBS. Rabbit serum (6 ml) was cycled through the columns five times consecutively, with the columns stripped and washed between runs as before. The final flow-through was passed three times through a neu phosphopeptide-Affi-Gel 10 column, and bound antibodies were eluted and dialyzed as before. They were then concentrated by filtration (Amicon Centriprep-30).

Example 2

Tyrosine-phosphopeptide-specific Antisera: Anti-pep (P) Antibody Specificity

Figure 1:
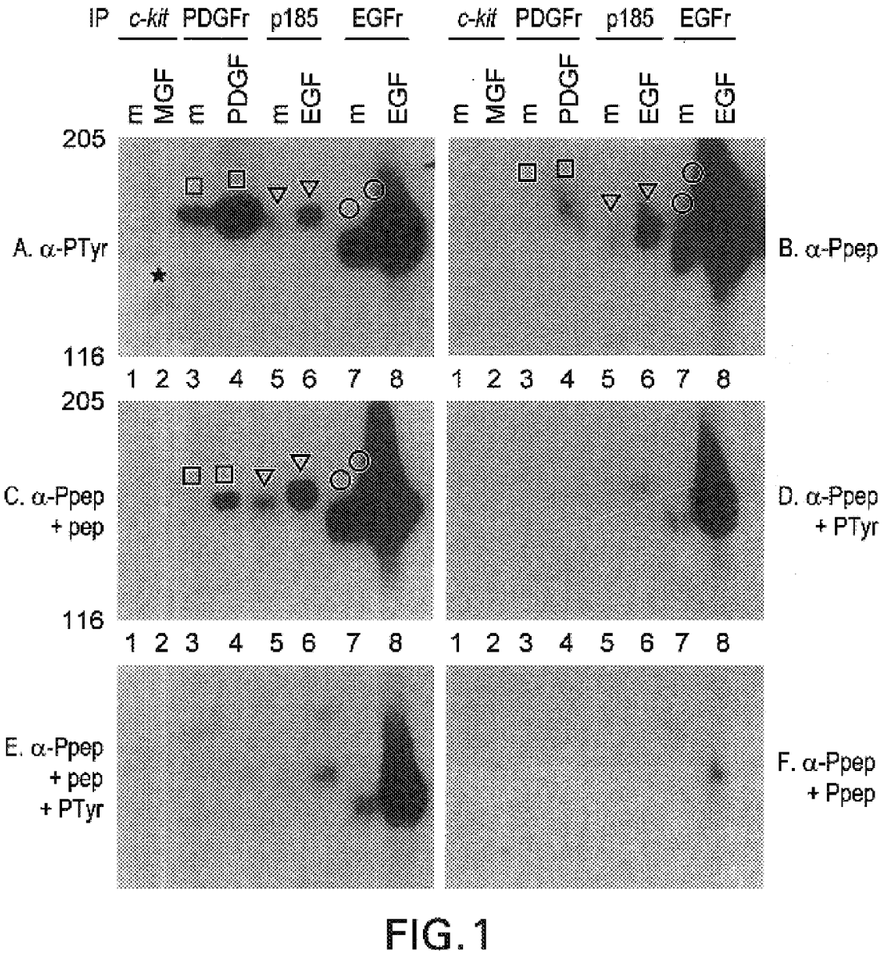

A. Materials & Methods. In the following experiments and in later examples, the following reagents and methods were used:
Cells. NIH 3T3, C127 (obtained from D. DiMaio, Yale University School of Medicine) (24), and FR3T3 are rodent fibroblast cell lines. SK-BR-3 human breast adenocarcinoma cells were obtained from American Type Culture Collection. They have amplified the neu gene and overexpress p185 (13, 25). A431 human epidermoid carcinoma cells have amplified the erbB (EGFr) gene, overexpress the EGFr, and express p185 at moderate levels (ref. 26; D.F.S., unpublished data). The 624 mel human melanoma cells were originally obtained from R. Zakut (National Cancer Institute) (27); pZen cells (originally obtained from L. Rohrschneider) are transfected with a c-fms-encoding plasmid and overexpress the colony stimulating factor 1 (CSF-1) receptor (28); Ya0vBix2NMA cells (29) were obtained from Barry M. Kacinski (Yale University School of Medicine).
Antibodies. Anti-c-neu Ab-3 monoclonal antibody (clone 3B5) was obtained from Oncogene Science; anti-EGFr monoclonal antibody 528 (30) was from H. Masui (Rockefeller University); anti-c-kit C terminus 212C (31) was from Yossi Yarden (Weizmann Institute); anti-platelet-derived growth factor (PDGF) receptor peptide antibody PR4 (32) was from Sara Courtneidge (European Molecular Biology Laboratory, Heidelberg); anti-c-met monoclonal antibody C28 (33) was from Donna Foletta and George Vande Woude (National Cancer Institute, Frederick, Md.); anti-insulin receptor AbPS (34) was from Robert Garafalo;. and polyclonal anti-Notch antibody was from Richard G. Fehon (Yale University School of Medicine). Polyclonal rabbit anti-Tyr(P) was raised against a synthetic copolymer of glycine, alanine, and phosphotyrosine and affinity-purified on a Tyr(P) column (35).
Growth Factors and Stimulation Experiments. Receptor stimulation experiments were similar to those described (12). EGF was used at final concentration of 100 ng/ml; mast-cell growth factor (MGF; supplied by Stewart D. Lyman, Immunex) was used at 100 ng/ml; PDGF (recombinant human BB form; GIBCO) was used at 10 ng/ml; insulin was used as insulin-transferrin-selenium premix (Collaborative Research; each at 25 ug/ml); recombinant human macrophage CSF-1 was used at 250 ng/ml; and scatter factor (a gift from Eliot Rosen, Yale University School of Medicine) was used at 500 units/ml.
Immunoblot Analysis. Proteins were resolved by electrophoresis in 7.5% polyacrylamide/0.175% N,N'-methylenebisacrylamide Laemmli gels, transferred to nitrocellulose (BiTrace NT; 0.45 um), and analyzed on an immunoblot as described (41). Antibodies were detected using $^{125}$I-labeled protein A (ICN; 35 uCi/ug; 1 Ci=37 GBq).
B. Receptor Specificity of Anti-Pep(P). The anti-neu phosphopeptide serum [anti-Pep(P)] was purified by a series of adsorption and affinity steps as indicated above in Example 1. To determine whether the anti-Pep(P) serum had phosphopeptide specificity, we examined its reactivity with a series of hormone-activated receptor tyrosine kinases and substrates. Autoradiographic exposures were chosen so that p185 and EGFr signals would be equivalent or darker in anti-Pep(P) immunoblots relative to anti-Tyr(P) immunoblots to facilitate comparisons between anti-Pep(P) and anti-Tyr(P).
neu, p185 phosphoprotein. Anti-Pep(P) was tested on p185 isolated by immunoprecipitation from SK-BR-3 human breast adenocarcinoma cells. These cells have an amplified neu gene and express high levels of p185. p185 is basally tyrosine-phosphorylated in this cell line either as a result of overexpression (41) or autocrine stimulation (55) and can be further regulated by EGF (12, 13). p185 immunoprecipitated from SK-BR-3 cells was readily detected by immunoblot analysis with anti-Tyr(P) (FIG. 1A, lane 5). Anti-Pep(P) also detected p185 (FIG. 1B, lane 5). As expected, EGF stimulated p185 reactivity with anti-Tyr(P) (FIG. 1A, compare lanes 5 and 6). A similar increase in reactivity with anti-Pep(P) was observed (FIG. 1B and C, lanes 5 and 6; because of the distortion in FIG. 1B, comparisons are simplest between FIGS. 1A and C). This demonstrated that the anti-Pep(P) serum recognizes p185 phosphorylation rather than simply the abundance of p185 (which is unaffected by EGF) (6, 12) and is not merely a peptide-specific antibody. The immunoreactivity was not affected by preincubation of the serum with the nonphosphorylated neu peptide (FIG. 1C, lane 5) and only modestly affected by blocking with Tyr(P) (FIG. 1D) or with a mixture of the nonphosphorylated peptide and Tyr(P) (FIG. 1E) but was virtually eliminated by blocking with the phosphopeptide (FIG. 1F).
EGF receptor. The similarity in sequence of an EGFr autophosphorylation site and the immunizing peptide suggested that the anti-Pep(P) serum might also recognize the EGFr.

The anti-Pep(P) serum did recognize the EGFr in an EGF-dependent (tyrosine phosphorylation dependent) way (FIGS. 1B and C, lanes 7 and 8). The ratios of p185 and EGFr intensities were similar in anti-Tyr(P) and anti-Pep(P) immunoblots (FIGS. 1A and C, lanes 5–8).

MGF receptor. c-kit, the MGF receptor, was recognized by anti-Tyr(P) (FIG. 1A, lane 2). However, it was not visible on anti-Pep(P) immunoblots (FIGS. 1B and C, lanes 2). This demonstrated that anti-Pep(P) discriminates against the MGF receptor and is not merely an anti-Tyr(P) serum.

Figure 2:
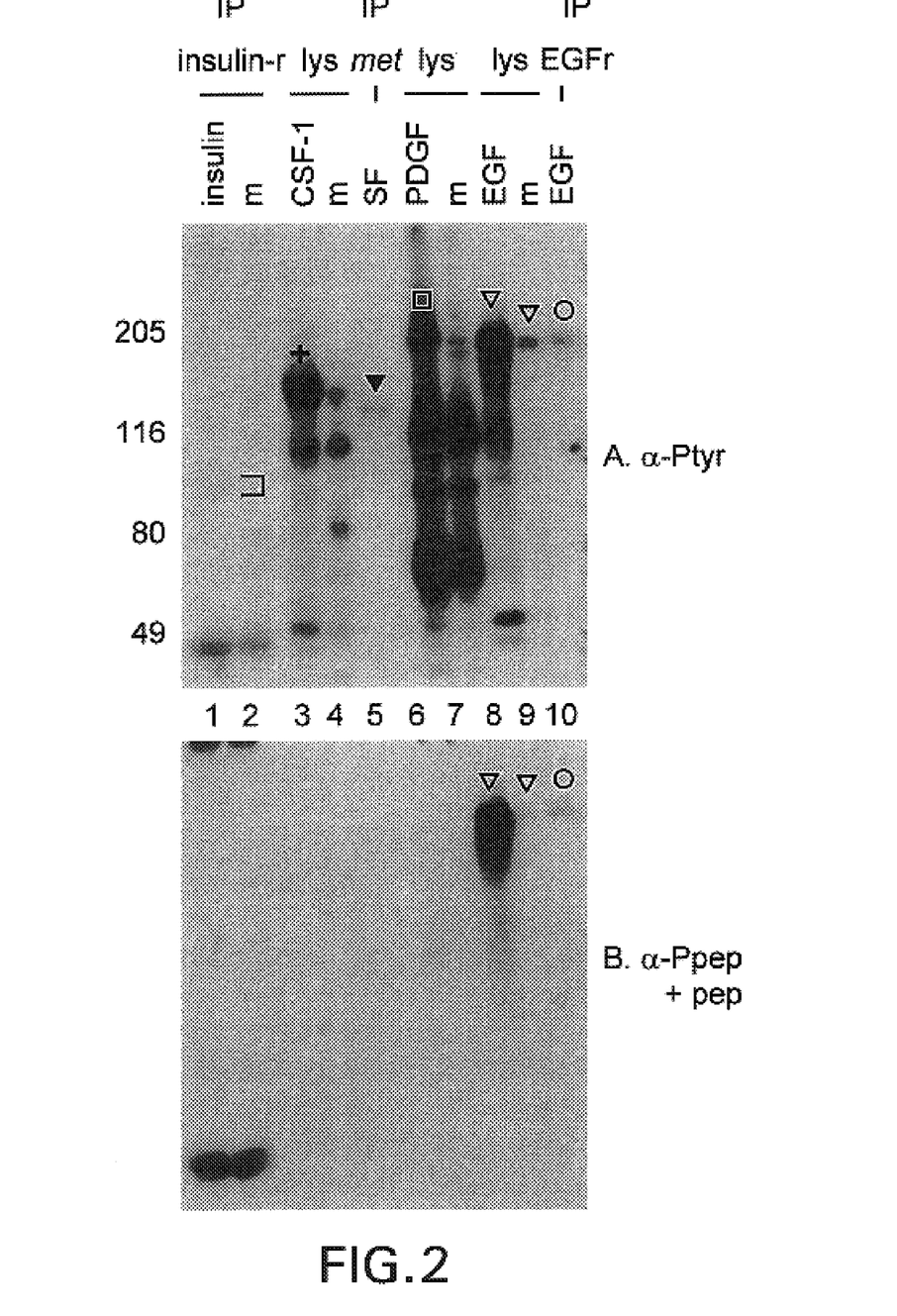

PDGF receptor. Similarly, the intensity of PDGF receptor bands was greatly reduced relative to the intensity of p185 and the EGFr in the anti-Pep(P) immunoblots (FIGS. 1A and C, lanes 3 and 4; FIG. 2, lanes 6).

Thus, using a simple general scheme, Applicants have produced a serum that specifically recognizes p185 and the EGFr in a phosphorylation-dependent manner.

Example 3

Tyrosine-phosphopeptide-specific Antisera: Anti-pep (P) Antibody Peptide Specificity Recognition of Substrates. We next determined whether the anti-Pep(P) serum discriminates against phosphorylated substrates. Protein lysates from CSF-1-treated cells (FIG. 2, lanes 3) and PDGF-treated cells (FIG. 2, lanes 6) contained many anti-Tyr(P) immunoreactive bands besides the receptors. The anti-Pep(P) serum failed to recognize most of the bands in these lysates. Moreover, anti-Pep(P) recognized p185, but not lower molecular weight substrates, in lysates of EGF-treated SK-BR-3 cells (FIG. 2, lanes 8). Anti-Pep(P) and anti-Tyr(P) reacted equivalently with p185 (FIG. 2, lanes 8 and 9) and the EGFr (FIG, 2, lanes 10). However, reactivity with c-met [the scatter factor receptor (FIG. 2, lane 5)], c-fms [the CSF-1 receptor (FIG. 2, lanes 3)], and the insulin receptor (FIG. 2, lanes 1) was greatly reduced or eliminated relative to reactivity with p185 and the EGFr.

This example and example 2 establish that anti-Tyr(P) antibodies can be produced that have peptide specificity. This specificity can be further defined by the use of monoclonal antibodies raised against tyrosine phosphopeptides, since the present antisera work establishes the existence of the appropriate epitopes. The method should be applicable for any protein for which tyrosine phosphorylation sites have been identified.

Example 4

Tyrosine-phosphopeptide-specific Antisera: Anti-pep (P) Antibody Sensitivity

Figure 3:
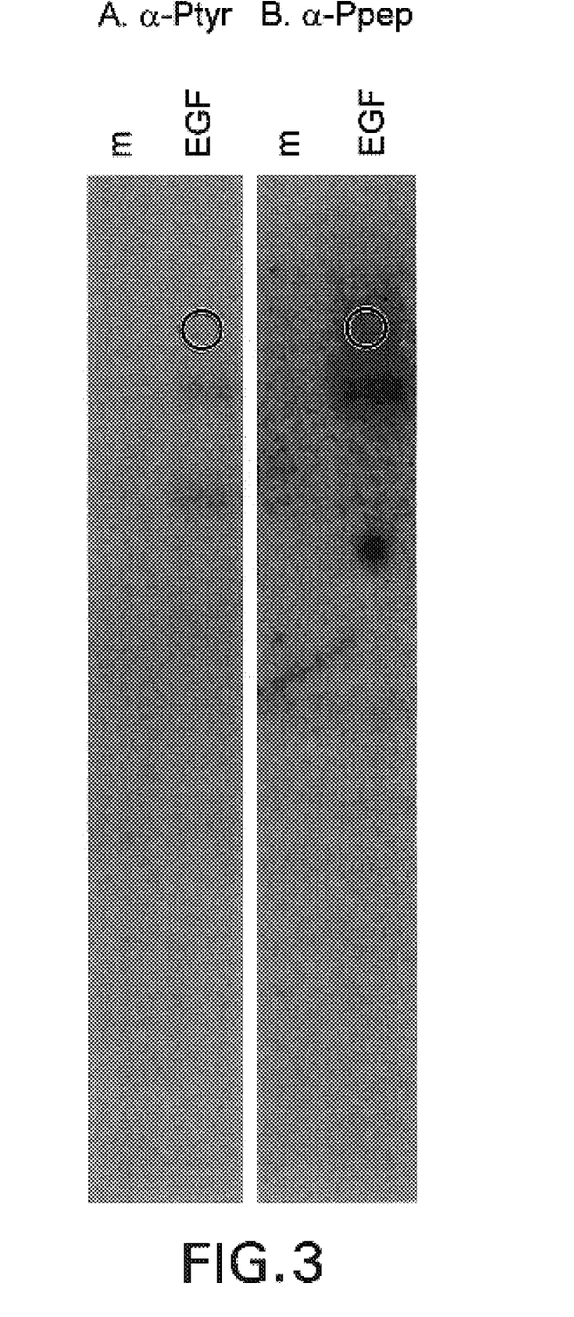

The anti-Pep(P) immunoblot analysis was sensitive enough to detect the EGF-stimulated EGFr (but not substrates) expressed at normal levels in lysates of FR3T3 fibroblasts (FIG. 3). Thus, the anti-Pep(P) sera recognizes p185 and the EGFr equally well. It is sensitive enough to recognize the tyrosine-phosphorylated EGFr at basal levels in rodent fibroblasts by immunoblot analysis and to recognize activated p185 by immunofluorescence at levels found in SK-BR-3 breast carcinoma cells (see Example 5, below). Greater sensitivity will be achieved with the use of mixtures of monoclonal antibodies that recognize the multiple autophosphorylation sites.

Example 5

Tyrosine-phosphopeptide-specific Antisera: Immunofluorescence Analysis

Figure 4:
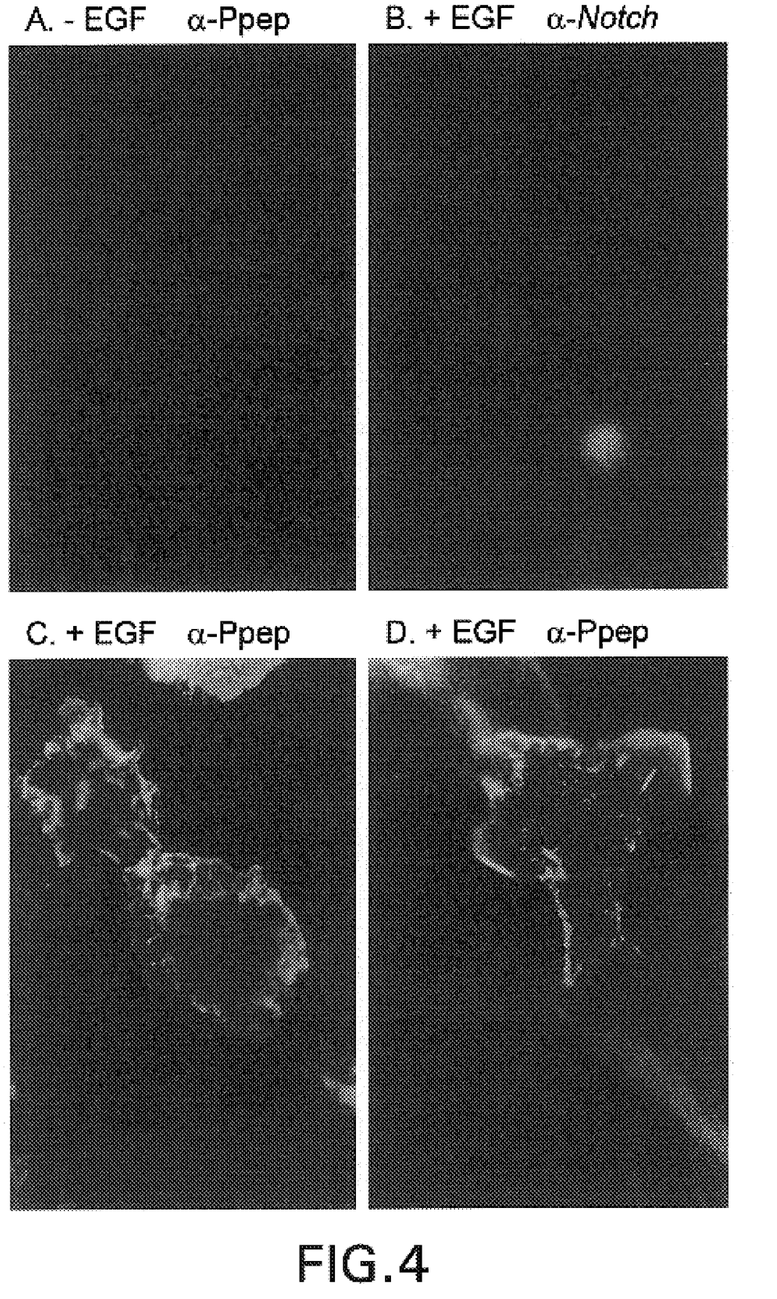
FIG. 4. Immunofluorescence of EGF-treated cells. A431 cells were mock-stimulated (A) or stimulated with EGF (B–D). Cells were permeabilized and visualized by indirect immunofluorescence with anti-Pep(P) (A, C, and D), or anti-Notch (B).

To determine whether these sera could be used in tissue-based assays, anti-Pep(P) was tested in immunofluorescence experiments. Indirect immunofluorescence was performed as described (42, 43) except that 1 mM sodium orthovanadate was used as a phosphatase inhibitor. Binding of rabbit anti-Pep(P) was detected with secondary biotinylated goat anti-rabbit IgG followed by rhodamine-conjugated avidin. Human A431 epidermoid carcinoma cells were stimulated with EGF and analyzed by indirect immunofluorescence (FIG. 4). Little staining was observed with mock-treated cells (FIG. 4A) by using anti-Pep(P). In contrast, bright fluorescence was observed for EGF-treated cells (FIGS. 4C and D). Such fluorescence was not seen when EGF-treated cells were probed with an irrelevant control serum raised against the Drosophila melanogaster Notch protein (FIG. 4B). Anti-Pep(P) immunofluorescence was blocked by pre-incubation with the phosphorylated, but not the nonphosphorylated, neu peptide (data not shown). Similar results were also obtained with SK-BR-3 cells (data not shown).

Example 6

Tyrosine-phosphopeptide-specific Antibodies Bind to Breast Carcinoma Specimens

Anti-phosphopeptide specific antibodies, anti-erbB-2 peptide antibodies and anti-phosphotyrosine antibodies were used to stain a panel of roughly 100 frozen breast carcinoma specimens using immunohistochemistry and detection with an alkaline phosphatase-based system (data not shown). The staining with the anti-phosphopeptide antibody was specific and varied independently of staining by the other two antibodies. There was an inverse correlation of. anti-phosphopeptide antibody staining with progesterone receptor, a marker for tumor aggressiveness (increased progesterone receptor levels correlate with decreased tumor aggressiveness). The anti-phosphopeptide antibody was also effective in staining paraffin-embedded sections of breast tumors by immunohistochemistry using a horseradish peroxidase-based system.

Example 7

Tyrosine-phosphopeptide-specific Monoclonal Antibodies

Mice were immunized with phosphopeptide linked to Keyhole Limpet Hemocyanin as a carrier protein. The peptide containing Try(P)-1248 is the same peptide used in Example 1. Spleen cells were collected and hybridomas were produced by fusion with a myeloma cell line according to standard techniques. Approximately 1200 culture supernatants were screened by ELISA for reactivity with plates coated with neu phosphopeptide conjugated to bovine serum albumin. 68 positives were screened for the desired reactivity by eliminating those that reacted with the nonphosphorylated neu peptide, a phosphorylated EGFr peptide, or a phosphorylated src Tyr(P)-416 peptide. 10 hybridomas that made it through the screen were cloned and 5 continued to produce antibodies. Of these, all show the original pattern of ELISA reactivity in the panel of peptides just described. At least one antibody, #2, shows neu specificity in immunoblots, does not recognize the EGF receptor, and stains a subset of breast carcinoma specimens that overexpress neu (data not shown).

Example 8

Anti-phospho-src Tyr 416 Specific Antibodies:

Phospho-Src Tyr 416 antibody: Phosphorylation of Src at Tyr-416 is associated with activation of Src. In order to obtain antibodies that would specifically recognize activated forms of Src in tumor tissues, we immunized rabbits with a phosphopeptide corresponding to residues 409–423 of c-src phosphorylated at Tyr-416[Arg-Leu-Ile-Glu-Asp-Asn-Glu-Tyr (p) -Thr-Ala-Arg-Gln-[$^{14}$C]Gly-Ala-Lys] coupled to Bovine Serum Albumin. We passed the peak titer sera through columns of BSA-agarose (to remove anti-carrier antibodies), phosphotyrosine-Affigel (to remove nonsequence-specific antiphosphotyrosine antibodies), and the corresponding nonphosphorylated Src 409–423 peptide linked to Affigel (to remove antibodies that cross-react with the nonphosphorylated peptide). The antibodies were then affinity purified on a column of the phosphotyrosine-416 peptide. Monoclonal antibodies to the phosphorylated and nonphosphorylated peptides are being generated.

There are several reasons to believe that activation of Src family kinases may correlate with the prognosis of breast cancer patients. They are downstream targets activated by multiple growth factor receptors, including neu. Our observations that activated Src binds the neu C-terminal phosphopeptide raises the possibility that the phosphorylated Neu C-terminus may directly activate c-Src in those cells in which neu is overexpressed and activated. Moreover, transgenic mice harboring a mouse mammary tumor virus-driven polyoma middle T oncogene develop mammary tumors.

The Src protein is the predominant tyrosine kinase activated in many breast carcinomas. Furthermore, activation of Src is generally an early event in the genesis of colon cancers. Activation of Src in colonic neoplasms occurs in the absence of mutations of the src gene, indicating that other cellular factors are responsible for the increased activity of Src in colon cancer tissues.

Breast cancer specimens will be screened with the above phospho-src specific antisera and monoclonal antibodies to determine whether a disease correlation with prognostic significance can be identified.

Example 9

Other Phosphopeptide Specific Antibodies

Phosphorylated peptides were synthesized by standard Merrifield procedures with the following modifications: N' tert-butyloxycarbonyl (Boc) derivatives of the C-terminal amino acids linked to chloromethylated polystyrene (Merrifield resins, Bachem) resins rather than phenylacetamidomethyl (PAM) resins were used to facilitate phosphopeptide cleavage. Phosphotyrosine was incorporated as Boc-o-(dibenzylphosphono)-L-tyrosine (Peninsula Laboratories). Boc amino acids were coupled either as symmetrical anhydrides or active esters. Methionine was incorporated as Boc-L-methionine sulfoxide. Phosphorylated peptides were cleaved with trifluoromethanesulfonic acid (TFMSA) as follows: Each gram of phosphorylated peptide resin (previously dried under vacuum) was stirred for 10 min at 0° C. with 2 ml m-cresol, and 2 ml dimethylsulfide. An Ice-cold mixture of 4 ml of TFMSA (Aldrich or Applied Biosystems; TFMSA ampule was opened immediately before use and kept under nitrogen) and 10 ml of trifluoroacetic acid (TFA, Applied Biosystems) was added slowly with stirring. The reaction was stirred under a nitrogen atmosphere for 4 hr at 0° C. The cleaved phosphopeptides were precipitated with methyl tert-butyl ether at −30° C., dissolved in 10–50% acetic acid and lyophilized several times from water. Methionine sulfoxide-containing peptides were dissolved in water, adjusted to pH 7 with NaOH and reduced by overnight stirring at 37° C. with N-methylmercaptoacetamide (20% vol/vol) prior to purification. Nonphosphorylated peptides corresponding to each of the phosphorylated peptides were also synthesized.

The following other phosphoamino acid-containing peptides were synthesized:

c-Fgr residues 517–529 phosphorylated at Tyr-523 [Thr-Ser-Ala-Glu-Pro-Gln-Tyr(P)-Gln-Pro-[14C]Gly-Asp-Gln-Thr]

Raf-1 residues 253–264 phosphorylated at Ser-259 [(Lys)-Gln-Arg-Gln- Arg-Ser-Thr-Ser(P)-Thr-Pro-Asn-Val-His]

Lck residues 497–509 phosphorylated at Tyr-505 [Phe-Phe-Thr-Ala-Thr-Glu-Gly-Gln-Tyr(P)-Gln-Pro-Gln-Pro]

PDGF β residues 745–755 phosphorylated at Tyr-751 receptor [Lys-Asp-Glu-Ser-Val-Asp-Try(P)-Val-Pro-Met-Leu-Asp-Met-Lys]

PDGF β residues 851–863 phosphorylated at Tyr 857 receptor [Ile-Met-Arg-Asp-Ser-Asn-Tyr(P)-Ile-Ser-Lys-[14C]Gly-Ser-Thr]

Using the methods of the Applicants' invention, these peptides will now be used to generate polyclonal or monoclonal antibodies, which will be positively and/or negatively selected to remove undesired cross-reactivities to generate phosphopeptide-specific antibodies against these oncogenic proteins and growth factor receptors.

Applications. The significance of phosphopeptide-specific anti-Tyr(P) sera lies in their ability to identify and quantify subsets of individual tyrosine kinases and substrates that differ in phosphorylation state and hence functionality. Phosphorylation at a particular site can correlate with enzymatic activation (e.g., receptor tyrosine kinases, mitogen-activated protein kinases, phospholipase C-γ), or inactivation (e.g., [Tyr$^{527}$]c-src and pp$^{34cdc2}$) (44, 45, 57, 58, 59). Peptide specific antibodies have been produced that specifically recognize the C-terminal src phosphorylation site and identity an inactive subset of src molecules (60).

Anti-tyrosine phosphopeptide sera will greatly simplify cell-free analysis of tyrosine phosphorylation. Phosphorylation of p185 and EGFr can be detected in unfractionated lysates with the substrate phosphorylations eliminated so that the protein extracts can be assayed directly by ELISA or dot blot analysis. Sera that discriminate among various phosphorylation sites in a single protein will facilitate analysis of the temporal order of phosphorylations and make possible physical separation of differentially phosphorylated populations that may have different functional properties. Similarly, the application of these sera to immunofluorescence assays will reveal the subcellular localization of these subpopulations.

The most significant application for tyrosine phosphopeptide-specific antisera will be the measurement of phosphorylation in tissues. The anti-phospho-neu sera are sensitive enough to monitor p185 phosphorylations in SK-BR-3 cells, which represent breast adenocarcinomas with an amplified and overexpressed Neu gene. It should, therefore, be possible to use the same sera for analysis of p185 activity in this subset of clinical specimens and determine the clinical correlates of p185 activation. This analysis, we predict, will reveal a substantially stronger prognostic significance for p185 than has been evident from present studies concerning p185 abundance. It is probable that substrate tyrosine phosphorylations will also have strong clinical correlates since the substrates represent integration points for the activity of multiple receptors.

Finally, these sera will be important tools in analyzing the normal function of tyrosine kinases. Receptors such as p185 and the EGFr have broad tissue distribution but probably have specialized functions based on temporally and spatially precise production of their ligands (61). Immunohistochemistry of tissues from mature and developing organisms using peptide-specific anti-Tyr(P) will reveal the locale and time at which specific tyrosine kinases are activated. This will lead to a much deeper understanding of the physiological roles of these important proteins.

References

1. Cantley, L. C., et al. (1991) Cell 64,281–302.
2. Ross, A. H., et al. (1981) Nature (London) 294, 654–656.
3. Frackelton, A. R., Jr., et al.(1983) Mol. Cell. Biol. 3, 1343–1352
4. Stern, D. F. (1991) Methods Enzymol. 198, 494–501.
5. Padhy, L. C., et al. (1982) Cell 28, 865–871.
6. Stern, D. F., et al. (1986) Mol. Cell Biol. 6, 1729–1740.
7. Wen, D., et al. (1992) Cell 69, 559–572.
8. Holmes, W. E., et al. (1992) Science 256, 1205–1210.
9. Bargmann, C. l., et al. (1986) Nature (London) 319, 226–230.
10. Coussens, L., et al. (1985) Science 230, 1132–1139.
11. Yamamoto, T., et al. (1986) Nature (London) 319, 230–234.
12. Stern, D. F. & Kamps, M. P. (1988) EMBO J. 7, 995–1001.
13. King, C. R., et al. (1988) EMBO J. 7, 1647–1652.
14. King, C. R., et al. (1985) Science 229, 974–976.
15. Slamon, D. J., et al. (1989) Science 244, 707–712.
16. Park, J.-B., et al. (1989) Cancer Res. 49, 6605–6609.
17. D'Emilia, J., et al. (1989) Oncogene 4, 1233–1239.
18. Paik, S., et al. (1990) J. Clin. Oncol. 8, 103–112.
19. van de Vivjer, M. J., et al. (1988) N. Engl. J. Med. 319, 1239–1245.
20. Anbazhagan, R., et al. (1991) Ann. Oncol. 2, 47–53.
21. McCann, A., et al. (1990) Cancer 65, 88–92.
22. Clark, G. M. & McGuire, W. L. (1991) Cancer Res. 51, 944–948.
23. Wildenhain, Y., et al. (1990) Oncogene 5, 879–883.
24. Petti, L., et al. (1991) EMBO J. 10, 845–855.
25. Kraus, M. H., et al. (1987) EMBO J. 6, 605–610.
26. Ullrich, A., et al. (1984) Nature (London) 309, 418–425.
27. Funasaka, Y., et al. (1992) Mol. Biol. Cell 3, 197–209.
28. Rohrschneider, L. R., et al. (1989) Oncogene 4, 1015–1022.
29. Rosen, E. M., et al. (1991) Cancer Res. 51, 5315–5321.
30. Kawamoto, T., et al. (1983) Proc. Natl. Acad. Sci. USA 80, 1337–1341.
31. Yarden, Y., et al. (1987) EMBO J. 6, 3341–3351.
32. Kypta, R. M., et al. (1990) Cell 62, 481–492.
33. Bottaro, D. P., et al. (1991) Science 251, 802–804.
34. Herder, R., et al. (1986) J. Biol. Chem. 261, 2489–2491.
35. Kamps, M. P. & Sefton. B. M. (1988) Oncogene 2, 305–315.
36. Hazan, R., et al. (1990) Cell Growth Differ. 1, 3–7.
37. Merrifield, R. H. (1963) J. Am. Chem. Soc. 85, 2149–2154.
38. Stewart, J. M. & Young, J. D. (1984) Solid Phase Peptide Synthesis (Pierce Chemical Company, Rockford, Ill.).
39. Bergot, B. J., et al. (1986) Utility of Trifluoromethane Sulfonic Acid as a Cleavage Reagent in Solid Phase Peptide Synthesis (Applied Biosystems, Foster City, Calif.).
40. Kagan, A. & Glick, S. M. (1979) in Methods of Hormone Radioimmunoassay, eds. Jaffe, B. M. & Behrman, H. (Academic, New York), pp. 328–329.
41. Stern, D. F., et al. (1988) Mol. Cell. Biol. 8, 3969–3973.
42. Merwin, J. R., et al. (1990) J. Cell. Physiol. 142, 117–128.
43. McLean, I. W. & Nakane, P. K. (1974) Histochem. Cytochem. 22, 1077–1084.
44. Nishibe, S., et al. (1990) Science 250, 1253–1256.
45. Gould, K. L. & Nurse, P. (1989) Nature (London), 34, 39–45.
46. Downward, J. (1985) J. Biol. Chem. 260,14538–14546.
47. Kraus, M. H., et al. (1989) Proc. Natl. Acad. Sci. USA 86, 9193–9197.
48. Flores-Riveros, J. R., et al. (1989) J. Biol. Chem. 264, 21557–21572.
49. Tornqvist. H. E., et al. (1988) J. Biol. Chem. 263, 350–359.
50. Kazlauskas, A. & Cooper. J. A. (1989) Cell 58, 1121–1133.
51. Tapley, P., at al. (1990) Mol. Cell. Biol. 10, 2528–2538.
52. Kim, J. W., et al. (1990) J. Biol. Chem. 265, 3940–3943.
53. Payne, D. M., et al. (1991) EMBO J. 10, 885–892.
54. Pearson, R. B. & Kemp, B. E. (1991) Methods Enzymol. 200, 62–81.
55. Lupu, R., et al. (1992) Proc. Natl. Acad. Sci. USA 89, 2287–2291.
56. Czernik, A. J., et al. (1991) Methods Enzymol. 201, 264–283.
57. Courtneidge, S. A. (1985) EMBO J. 4, 1471–1477.
58. Cooper, J A., et al. (1986) Science 231, 1431–1434.
59. Anderson, N. G., et al. (1990) Nature (London), 343, 651–653.
60. Roussel, R. (1990) M.S. thesis (Univ. New Hampshire, Durham, N.H.)
61. Greenwald, I. & Rubin, G. M. (1992) Cell 68, 271–281.
62. Kohler & Milstein (1975) Nature 256, 495–497
63. Therapeutic Monoclonal Antibodies, eds. Borrebaeck, C. A. K. and Larrick, J. W.; Stockton Press, New York, 1990

Equivalents

The above examples are specific embodiments of the invention, and are not meant to limit the scope of the invention. Those skilled in the art will be able, through routine experimentation, to understand and generate other equivalents. Such equivalents are encompassed within the scope of the invention and the following claims.

We claim:

1. A preparation of polyclonal antiphosphopeptide-specific antibodies, wherein said antibodies are prepared by the process comprising:

(a) generating a polyclonal antiserum that is reactive with a predetermined phosphopeptide, the corresponding non-phosphopeptide and the corresponding phospho-amino acid by immunizing an animal with said phosphopeptide;

(b) selectively removing non-phosphopeptide-specific antibodies from said serum by adsorbing said serum with the nonphosphorylated form of said phosphopeptide linked to a solid support;

(c) selectively removing phosphoamino acid-specific antibodies from said serum by adsorbing said serum with the phosphoamino acid of said phosphopeptide linked to a solid support; and (d) recovering said antiphosphopeptide-specific antibodies;

where steps (b) and (c) can be performed in either order.

2. The preparation of claim 1, comprising steps (a) to (c) thereof and (d) selecting for said phosphopeptide-specific antibodies by adsorbing sad antibodies to said phosphopeptide linked to a solid support or to a phosphoprotein linked to a solid support, wherein said phosphoprotein is the source of said phosphopeptide; and (e) recovering said antiphosphopeptide-specific antibodies;

where steps (b), (c) and (d) can be performed in any order; but preferably step (d) occurs last.

3. The preparation or claim 2 comprising steps (a) to (d) thereof and (e) selectively removing carrier-specific antibodies from said serum by adsorbing said serum with the carrier of said phosphopeptide linked to a solid support; and (f) recovering said antiphosphopeptide-specific antibodies;

where steps (b), (c), (d) and (e) can be performed in any order, but preferably step (d) occurs last and step (e) occurs first.

4. The preparation of claim 1 wherein the phosphoamino acid is tyrosine.

5. The preparation of claim 4 wherein said phosphopeptide is from a tyrosine kinase.

6. The preparation of claim 5 wherein the tyrosine kinase is selected from the group consisting of Neu, Src, Fgr, Lck and PDGF receptor.

7. The preparation of claim 5 wherein the tyrosine kinase is the Neu tyrosine kinase.

8. The preparation of claim 1, wherein the phosphoamino acid is serine or threonine.

9. The preparation of claim 8, wherein said phosphopeptide is from a serine/threonine kinase.

10. The preparation of claim 9 wherein serine/threonine kinase is Raf-1.

11. An antigen binding fragment of said antiphosphopeptide specific antibodies of any one of claims 1–3.

12. A preparation of monoclonal antiphosphopeptide-specific antibodies, wherein said antibodies are prepared by the process comprising:

(a) immunizing an animal with a predetermined phosphopeptide, thereby producing antibodies that are reactive with said phosphopeptide, with a corresponding non-phosphopeptide and with a corresponding phosphoamino acid, and identifying individual clones which produce antibodies that bind to said phosphopeptide;

(b) screening said clones for production of non-phosphopeptide-specific antibodies by binding the antibodies produced by each of said clones to the nonphosphorylated form of said phosphopeptide linked to a solid support;

(c) screening said clones for production of phosphoamino acid-specific antibodies by binding the antibodies produced by each of said clones to the phosphoamino acid of said phosphopeptide linked to a solid support; and (d) identifying those clones which produce antibodies that bind to said phosphopeptide but fail to bind to either said non-phosphopeptide or said phosphoamino acid; and (e) recovering said antiphosphopeptide-specific antibody from the clones identified by step (d);

where steps (b) and (c) can be performed in either order.

13. The preparation of claim 12, wherein the phosphoamino acid is tyrosine.

14. The preparation of claim 13, wherein said phosphopeptide is from a tyrosine kinase.

15. The preparation of claim 14, wherein said tyrosine kinase is selected from the group consisting of Neu, Src, Fgr, Lck and PDGF receptor.

16. The preparation of claim 14, wherein the tyrosine kinase is the Neu tyrosine kinase.

17. The preparation of claim 12, wherein said phosphoamino acid is serine or threonine.

18. The preparation of claim 17, wherein said phosphopeptide is from a serine kinase or a threonine kinase.

19. The preparation of claim 18, wherein the serine kinase is Raf-1.

20. An antigen binding fragment of said antiphosphopeptide specific antibodies of any one of claims, 12–19.

21. Isolated antiphosphopeptide antibodies that specifically bind to a phosphopeptide, or a protein containing said phosphopeptide, but are not specific for the corresponding non-phosphorylated peptide, or a protein containing said non-phosphorylated peptide, or for the phosphoamino acid of said phosphopeptide.

22. The antibodies of claim 21 wherein, said phosphopeptide is a phosphotyrosine phosphopeptide.

23. A method of preparing polyclonal antiphosphopeptide-specific antibodies, which comprises (a) generating a polyclonal antiserum that is reactive with a predetermined phosphopeptide, the corresponding non-phosphopeptide and the corresponding phosphoamino acid by immunizing an animal with said phosphopeptide;

(b) selectively removing non-phosphopeptide-specific antibodies from said serum by adsorbing said serum with the non-phosphorylated form of said phosphopeptide linked to a solid support;

(c) selectively removing phosphoamino acid-specific antibodies from said serum by adsorbing said serum with the phosphoamino acid of said phosphopeptide linked to a solid support; and (d) recovering said antiphosphopeptide-specific antibodies;

where steps (b) and (c) can be performed in either order.

24. The antibodies of claim 21, wherein said phosphopeptide is from a tyrosine kinase.

25. The antibodies of claim 24, wherein the tyrosine kinase is the Neu tyrosine kinase.

26. An antigen binding fragment of said antiphosphopeptide specific antibodies of any one of claims 21, 22, 24, and 25.

* * * * *